United States Patent [19]
Vance et al.

[11] Patent Number: 5,744,688
[45] Date of Patent: Apr. 28, 1998

[54] QUALITY CONTROL FOR BIOLOGICAL DECONTAMINATION AND STERILIZATION

[75] Inventors: Paula Vance; Alice Weissfeld, both of Houston, Tex.

[73] Assignee: Microbiology Specialists, Inc., Houston, Tex.

[21] Appl. No.: 725,612

[22] Filed: Oct. 3, 1996

[51] Int. Cl.$^6$ .................................................. C07B 33/00
[52] U.S. Cl. ............................ 588/205; 435/4; 435/31; 435/34; 435/810; 422/31; 422/61
[58] Field of Search ................................. 435/31, 34, 4, 435/810; 422/31, 61; 588/205

[56] References Cited

U.S. PATENT DOCUMENTS

| | | | |
|---|---|---|---|
| 4,169,123 | 9/1979 | Moore et al | 422/29 |
| 4,591,566 | 5/1986 | Smith | 435/291 |
| 5,077,007 | 12/1991 | Pearson | 422/3 |
| 5,078,965 | 1/1992 | Pearson | 422/3 |
| 5,116,574 | 5/1992 | Pearson | 422/3 |
| 5,173,257 | 12/1992 | Pearson | 422/3 |
| 5,322,603 | 6/1994 | Kameda et al. | 204/158.2 |
| 5,348,235 | 9/1994 | Pappas | 241/41 |
| 5,366,872 | 11/1994 | Hird et al. | 435/31 |
| 5,372,929 | 12/1994 | Cimino et al. | 435/6 |

OTHER PUBLICATIONS

Technical Assistance Manual: State Regulatory Oversight of Medical Waste Treatment Technologies; Apr. 1994; A Report of the State and Territorial Association on Alternate Treatment Technologies.

Manual of Clinical Microbiology; Sixth Edition; ASM Press, Washington, DC; pp. 92 and 93 (no date).

Clinical and Pathogenic Microbiology; Second Edition; Mosby Press; pp. 69, 96, and 97 (no date).

*Primary Examiner*—Arun S. Phasge
*Attorney, Agent, or Firm*—Pravel, Hewitt, Kimball & Krieger

[57] ABSTRACT

The present invention relates to new methods and new destruction-resistant materials for simple and routine quality control measurement of the effectiveness of biological decontamination and sterilization processes that utilize at least one step involving physical disruption of treated wastes, where such physical disruption would destroy conventional, non-destruction-resistant quality control means. Quantitative and qualitative analysis is provided.

10 Claims, 1 Drawing Sheet

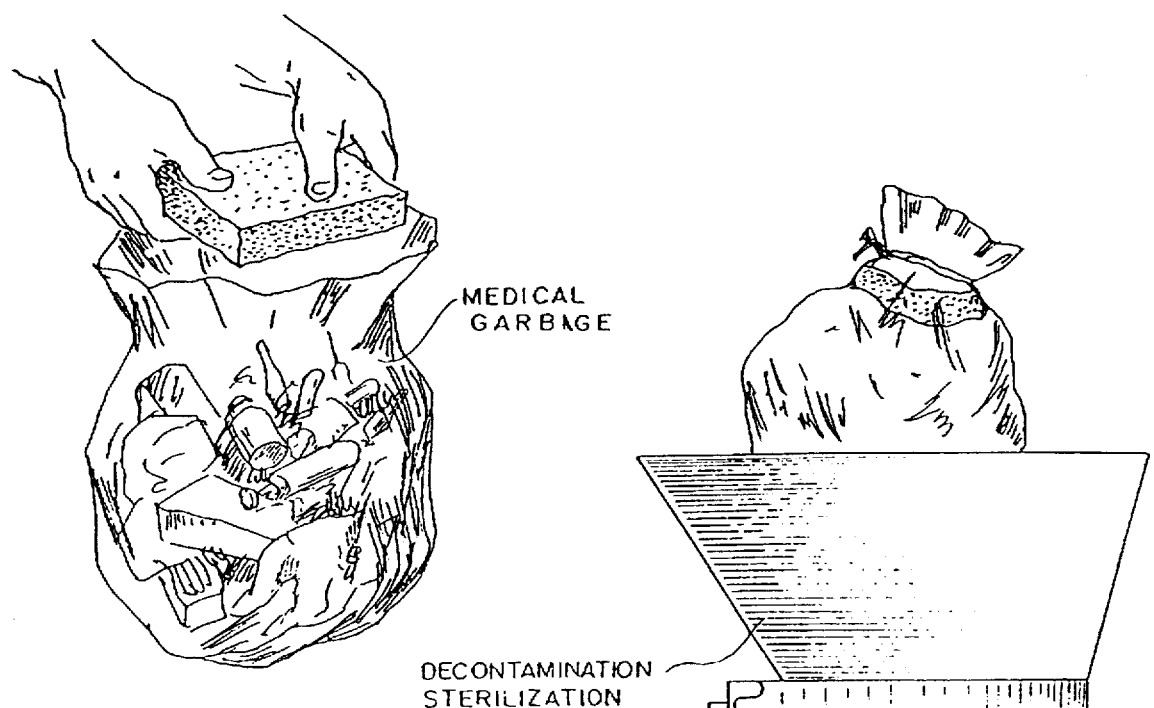
FIG.1
FIG.2
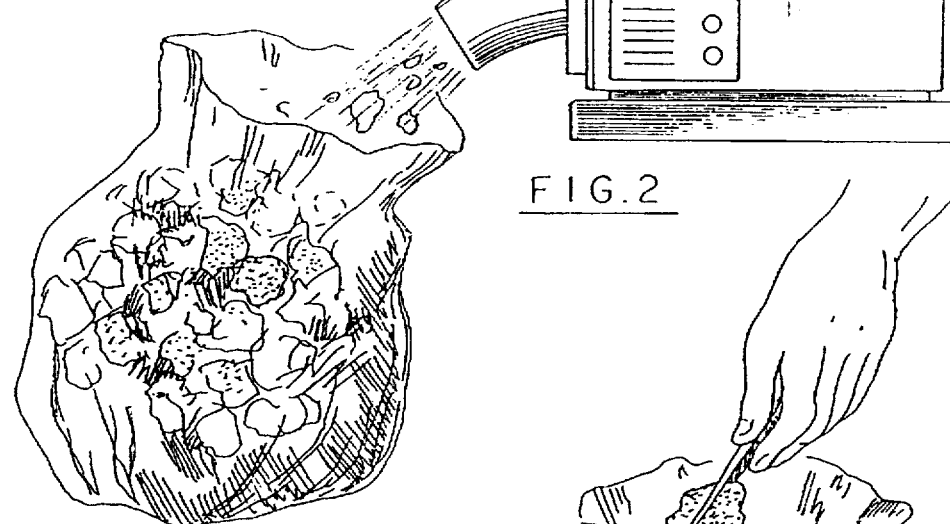
FIG.3
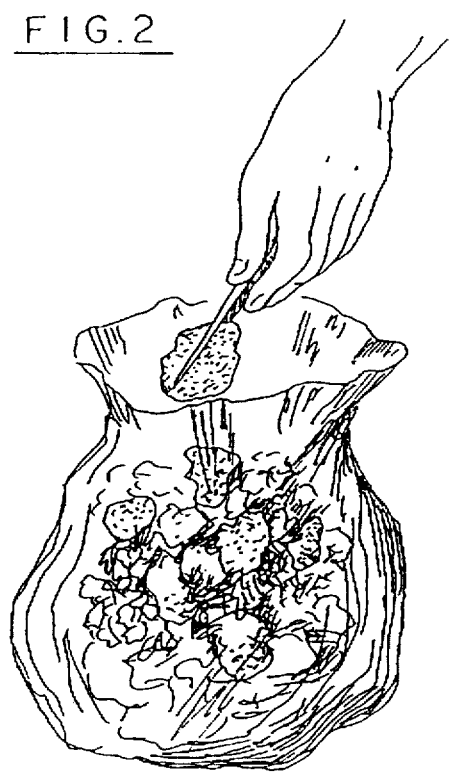
FIG.4

QUALITY CONTROL FOR BIOLOGICAL DECONTAMINATION AND STERILIZATION

BACKGROUND OF THE INVENTION:

1. Field of the Invention

The present invention relates to new methods and new materials for measuring the effectiveness of biological decontamination and sterilization processes, and thus, relates to new methods and new materials for quality control assurance in biological decontamination and sterilization systems. More particularly, the present invention relates to new methods and new materials for effective, simple and routine quality control assurance in biological decontamination and sterilization systems that utilize at least one step involving physical disruption of treated wastes, where such physical disruption would destroy conventional, non-destruction-resistant quality control means, the present invention providing materials and methods for quality control that are resistant to physical disruption in biological decontamination and sterilization systems. Still more particularly, the present invention relates to the use of any biological organism, seeded on any destruction-resistant medium, used as a quality control means for any type of decontamination and/or sterilization procedure that would otherwise destroy a traditional, nondestruction-resistant quality control means.

2. General Background

Each year hospitals, laboratories, clinics and medical offices produce hundreds of thousands of tons of biomedical, infectious wastes. The safe, effective and inexpensive disposition of this waste has become a major issue of the late twentieth century. Ineffective and inappropriate disposal practices have led to dangerous and highly publicized incidents such as the discovery of infectious medical waste washed up on beaches of oceans and lakes, as well as well as the discovery of infectious wastes in ordinary trash containers in public areas. In response to such incidents, federal and state governments have acted to tightly regulate the disposition of infectious wastes, including the imposition of requirements mandating quality control assurances for biological waste treatment systems.

Historically, most infectious waste has been treated by incineration. However, recent studies performed on emissions generated from the combustion of medical waste, even from facilities equipped with advanced air pollution control equipment, have demonstrated consistent emission of priority metals, acid gases, and carcinogenic organics such as 2, 3, 7, 8 furans and dioxin. (United States Environmental Protection Agency, *Hospital Waste Combustion Study*, Dec., 1988). Such emissions from incineration have given rise to problems concerning compliance with the Federal Clean Air Standards Act which, as a result, have often raised to prohibitive levels capital and operating costs associated with incineration of biomedical wastes. Further, increased public awareness and opposition to incineration, especially in populous areas, and stricter licensing requirements have made many infectious waste generators, and their regulators, reexamine their options for the treatment and disposal of infectious medical and laboratory waste. (See, e.g., P. R. Murry, EIC, *Manual of Clinical Microbiology*, Sixth Ed., pgs. 92–93).

Another method traditionally used for decontamination of infectious wastes involves steam sterilization in autoclaves. However, autoclaves are not appropriate for economically treating large volumes of infectious waste. Further, additional complications with traditional steam sterilization techniques often arise because traditional steam sterilization techniques do not physically disrupt the treated waste. For example, the effectiveness of steam sterilization can be adversely affected by the physical nature of the waste to be treated (since the effectiveness of steam sterilization depends upon factors such as the density, physical state and size, and organic content of the waste), leading to problems in assuring effective quality control where autoclaved wastes are not physically disrupted. And, because autoclaves do not change the inherent visual appearance of treated waste, uncertainty and fear frequently arises among persons responsible for handling the treated waste, leading to, inter alia, many reported cases of autoclaved waste being rejected at landfills.

Hence, there is a need to develop alternative infectious waste disposal systems and technologies that solve, or reduce the problems presented by the traditional treatment systems of incineration and non-disruptive steam sterilization. To meet this need, the waste disposal industry developed a number of alternative infectious waste disposal systems that utilize a step of physical disruption of the waste as part of the treatment. Alternative waste disposal systems utilizing physical disruption steps avoid the pitfalls of both traditional non-disruptive, steam sterilization and incineration by both, respectively, i) enhancing the effectiveness of steam disinfection and sterilization and the identification of the treated product, and ii) eliminating dangerous emissions from waste incineration. (P. R. Murry, EIC, *Manual of Clinical Microbiology*, Sixth Ed., pgs. 93).

Some of the first alternative waste treatment systems produced involve mechanical-chemical treatment of infectious waste. Systems such as Medical SafeTEC, Inc.'s (Indianapolis, Ind.) Model Z1200 employ a high-speed hammer mill combined with a shredder to pulverize and shred waste material prior to exposing the waste to chemical decontamination agents such as sodium hypochlorite. In these systems, once shredded and pulverized, the waste is mixed with a decontaminant in hoppers and/or screw agar conveyors where it is treated and subsequently dried. The final, treated waste product consists of the decontaminated, shredded and pulverized waste in a dry or fluid-expressed state.

Other alternative infectious waste treatment systems utilize mechanical disruption combined with traditional steam sterilization. For example, the Roland biomedical waste treatment system, S.A.S.-1, (S.A.S. Systems, Inc., Houston, Tex.) shreds and then sterilizes infectious waste in an enclosed unit that operates as an autoclave and shredder. Other alternative infectious waste treatment systems utilizing mechanical and thermal treatment shred waste and then disinfect it with alternative sources of heat, such as, for example, dry heat (BioMed Continuous Thermal Disinfection Unit, BioMed Waste Systems, Inc., Boston, Mass.), microwaves (ABB Sanitec Microwave Disinfection System, ABB Environmental Services, Inc., Roseland, N.J.), and low frequency radio waves (Stericycle Electrothermal Deactivation System, Stericycle, Inc., Deerfield, Ill.). In all these cases, the final, treated waste product consists of decontaminated, shredded waste in a dry or fluid-expressed state.

Monitoring the effectiveness of disinfection in infectious waste disposal systems is, of course, of paramount importance. Numerous state and federal regulations address the need for both diagnosic and routine quality control in biological decontamination systems. (See Id.) However, prior to the instant invention, quality control systems for routine use in biological decontamination systems were designed for use only with the traditional non-destructive decontamination and sterilization means discussed above. Importantly, these traditional quality control means were, and are, not resistant to physical disruption. As a result, traditional quality control means are incompatible with newer, waste-disrupting decontamination means since, in practice, such means are destroyed in the treatment process when the waste is treated with the physical disruption step(s).

Traditional, nondestruction-resistant quality control means for steam sterilization include, for example, glass and/or plastic ampules. (See, for example, Attest Biological Indicator, manufactured by 3M Health Care, St. Paul, Minn. 55144-1000. These ampules contain a given number of viable microorganisms either in vegetative state, or, as heat resistant endospores. As a means of routine quality control, an ampule is added to the waste to be treated. After treatment, the ampule is recovered, activated and the contents cultured. A determination of the viability of the contents of the ampule post sterilization and/or decontamination provides the means for quality control.

While these ampule-type means for quality control work well for traditional nondestruction-type waste treatment systems, they are wholly incompatible with modern destruction-type waste treatment systems. This is because the fragile ampule would be broken open during processing of the waste, making it impossible to recover the contents for subsequent determination of viability. Further, because modern waste disposal systems frequently treat continuous streams of waste, rather than batches, and because the waste is mixed upon treatment, it would be difficult, if not impossible to locate an ampule in the waste stream, even if it managed to remain uncrushed during treatment.

Another type of traditional, nondestruction-resistant quality control means for steam sterilization includes, for example, a small strip of material impregnated with bacterial spores. See, for example, SPORDEX®-SPORDI® Biological Indicators, manufactured by AMSCO International, Apex, N.C. 27502. These small strips of material contain a given number of viable microorganisms impregnated on the medium as heat resistant endospores. As a means of routine quality control, an impregnated strip of material is added to the waste to be treated with steam. After treatment, the material is recovered and cultured. A determination of the viability of the contents of the strip post sterilization and/or decontamination provides the means for quality control.

While these impregnated strip-type means for quality control work well for traditional nondestruction-type waste treatment systems, they, like ampules, are also wholly incompatible with modern destruction-type waste treatment systems. This is because the strips would be lost and/or torn into pieces during processing of the waste, making it impossible to recover the contents for subsequent determination of viability. Further, as with ampules, because modern waste disposal systems frequently mix waste upon treatment, it would be difficult, if not impossible to locate a small strip in the treated waste stream.

Thus, while the advent of alternative infectious waste treatment systems involving physical disruption of waste has brought an answer to many of the problems posed by traditional waste treatments, prior to the instant invention, there remained a great need for an accurate, simple and inexpensive means for providing routine quality control for these new waste-disrupting treatment systems. (See, e.g., *Technical Assistance Manual: State Regulatory Oversight of Medical Waste Treatment Technologies*, Apr. 1994, A Report of the State and Territorial Association on Alternate Treatment Technologies, pg. 1).

In this article, inter alia, recognizing the need for quality control in non-traditional disruptive-type alternate medical waste treatment technologies, the several states that had actively participated in programs authorized under the federal Medical Waste Tracking Act of 1988 organized into an association known as the State and Territorial Association on Alternate Treatment Technologies ("Association"). In 1994, the Association produced the *Technical Assistance Manual: State Regulatory oversight of Medical Waste Treatment Technologies*, which is hereby incorporated by reference in its entirety. This manual outlines both the need for quality control in "alternate" waste treatment systems ("alternate" being defined as "other than non-destruction-type steam sterilization or incineration," see pg. 1) and goals for quality control assays.

The manual sets forth, inter alia, i) a definition of the level of recommended microbial inactivation; ii) establishment of defined pathogen surrogates for microbial inactivation evaluation (including vegetative pathogen surrogates and bacterial spore formers); iii) formulae for enumeration for efficacy testing protocol quantification; and iv) development guidelines for approval of specific treatment processes and specific testing protocols.

However, and significantly, the manual was unable to propose specific recommended methods and materials for routine quality control in "alternate" (destruction-type) waste disposal systems. Instead, and in recognition of the long felt but unresolved need for such quality control means, the manual implored workers in the technical field to try to conceive of a workable, destruction-resistant quality control means (like the instant invention) for non-tradition decontamination systems.

While, as discussed in more detail below, the manual recognized the need for a destruction-resistant means to easily and routinely quantitate the effectiveness of alternate decontamination procedures, and the manual proposed microorganisms to be used with such procedures, guidelines to be followed when practicing such procedures, and goals of such procedures, importantly, the manual was unable to propose or suggest a suitable destruction resistant material and method for routine use.

In answer to the needs of the prior art, and those emphasized by the Alternate Treatment Technologies manual, the instant invention provides methods and destruction-resistant materials for inexpensive, simple and routine analysis of quality control of biological decontamination and sterilization systems utilizing alternative infectious waste disposal systems that physically disrupt waste upon treatment.

Briefly, the instant invention relates to a novel method and a product for quality control in alternative, destruction-type biological decontamination and sterilization processes. The invention relates the use of a biological organism, seeded on any destruction-resistant medium, used as a quality control means for any type of decontamination and/or sterilization procedure that would otherwise destroy a traditional, nondestruction-resistant quality control means. In one embodiment of the invention, for example, destruction-resistant sponges seeded with in a known number and type of bacteria, or spores, are used as a routine quality control means for alternate biological decontamination and/or sterilization processes. In such an embodiment, the bacteria/spore-seeded destruction-resistant sponge is added to the waste to be treated and then is processed along with the waste. The sponge material is then recovered from the treated waste where it can easily be visually and/or tactilely identified and removed from the waste stream. Following established protocols, (for example, those outlined in the *Oversight of Medical Waste Treatment Technologies Manual*) the number of viable bacteria associated with the recovered sponge material is determined (for example, by culturing and quantitating the number of viable organisms recovered) and compared relative to an untreated, control sponge and/or the sponge before treatment. A calculation of the reduction in viable bacteria between the seeded sponge and the treated sponge is then used to easily assess (again, for example, as per the guidelines of the Technical Assistance Manual) the quality, or effectiveness, of the biological decontamination process. In another similar embodiment, a destruction-resistant sponge seeded with a known number and type of microorganisms is added to a waste treatment system and recovered post treatment, and then the recovered sponge is cultured for the presence of any growth of the seeded organisms; the results producing an all-or-none qualitative evaluation of the effectiveness of the waste decontamination and/or sterilization system. Further descriptions of the preferred embodiments of the present invention are discussed below in the section entitled Detailed Description of the Preferred Embodiment.

While other patents have disclosed the assaying of waste treated by alternative destruction-type decontamination processes, these have been only for one-time-only/non-routine means of determining the efficacy of such systems, no known patents, or other publications, disclose the instant invention's use of an organism-seeded destruction-resistant material for carrying and recovery of "seed" organisms as a convenient, inexpensive and routine test for quality control in decontamination and/or sterilization procedures that physically disrupt the treated waste.

U.S. Pat. No. 5,372,929 to Cimino et al. discloses methods for measuring pathogen inactivation particularly in blood and blood products after photochemical decontamination. The measuring methods disclosed in the patent are drawn toward biochemical tests of the inhibition of template-dependent enzymatic synthesis. The Cimino et al. patent discloses a very different means for measuring the inactivation of organisms than does the instant invention. Further, the Cimino et al. patent appears drawn only to use with small scale decontamination processes, such as the decontamination of blood and blood products. Unlike the instant invention, it appears unlikely that the method of Cimino et al. would be practical for measuring inactivation of pathogens in large scale decontamination processes, such as the decontamination of hospital wastes.

U.S. Pat. Nos. 5,078,965 and 5,077,007 to Pearson disclose a process and apparatus for the batch treatment of infectious waste material in a fluidized bed reactor utilizing gas oxidation. While the patents disclose the use of a pretreatment inoculum of a know number and type of infectious organisms, and the subsequent culturing and enumeration of the organisms that are left after treatment as a means of determining the biological inactivation, the patents do not disclose the instant invention's means of providing a bacteria-seeded sponge for routine quality control of decontamination processes. The patents also fail to disclose the instant invention's ease of recovery of the seeded organisms. Further, the patents only disclose the removal of "seed" organisms from the liquid state of the wastes; no quality control is disclosed for checking the final "dewatered" residue.

U.S. Pat. Nos. 5,116,574 and 5,173,257 to Pearson disclose a process and apparatus for continuously treating infectious waste. Like Pat. Nos. 5,078,965 and 5,077,007 issued to Pearson and discussed above, Pat. Nos. 5,116,574 and 5,173,257 disclose only the experimental use of a liquid inoculum of infectious organisms. The patents fail to disclose the use of an organism-seeded sponge for routine quality control in decontamination processes.

U.S. Pat. No. 5,322,603 to Kameda et al. discloses a method of treating medical wastes with microwaves and hot air. Significantly, this patent discloses no means for assuring, or detecting, the killing of infectious organisms during the decontamination process.

U.S. Pat. No. 5,348,235 to Pappas discloses a medical waste disposal system wherein medical wastes are superheated such that no known pathogens can survive the operating temperatures of the system. Significantly, unlike the instant invention, the Pappas patent discloses no means for assuring, or detecting, the killing of infectious organisms during the treatment process.

Thus, while there is a recognized need in the field for a simple and economical means for routine quality control in alternate biological decontamination systems, issued patents related to alternative medical waste disposal systems do not disclose such a means. In fact, the only method for assessing effectiveness of alternative waste decontamination systems disclosed in the patents (other than the technically complex template-dependent enzymatic synthesis method of Cimino et al.) is the cumbersome assay method of providing a liquid inoculum with a known number of microorganisms to a defined batch of waste to be treated, treating the batch and then removing liquid samples from the treated liquid. Such protocols are difficult to perform, are not highly reproducible (due to the great dilution of recovered inoculum), cannot be used to evaluate dried (or liquid expressed) waste product (the actual waste product of the majority, if not all, commercial alternative waste treatment systems), and are not compatible with continuous run systems (the use of a liquid inoculum requires a treatment of a single batch of waste, rather than a continuous stream of waste as utilized in most alternate waste treatment systems).

Thus, as evidenced by both issued patents in the field and technical publications in the field, there is a need for a simple, economic and routine quality control method and means for use with alternative type, destruction-type medical waste treatment technologies.

SUMMARY OF THE PRESENT INVENTION

The present invention relates to new methods and materials for measuring pathogen inactivation in medical waste treatment technologies that utilize a waste-disrupting step.

It is therefore an object of the present invention to provide materials and methods for evaluating the decontamination efficiency of "alternate" infectious waste decontamination systems, "alternate" systems being defined as waste treatment decontamination systems utilizing a step of physical disruption of the treated waste.

It is an object of the present invention to provide materials and methods for inoculating waste to be treated with a number of microorganisms seeded in a destruction-resistant medium, adding such medium to the waste to be treated, processing and treating the waste containing the medium, recovering the medium from the waste and quantifying or qualifying the remaining viable organisms in or on the medium following treatment.

It is a further object of the present invention to provide a method and materials for quantitating the efficiency of decontamination by alternate waste disposal systems. In one embodiment, a destruction-resistant medium is seeded with a number of a specific type of organisms, added to waste and treated with waste, recovered from treated waste, and the remaining viable organisms associated with the medium quantitiated and compared with the number remaining on an identically seeded medium, identically treated but for the decontamination step of the decontamination process, or compared to the known number of organisms originally on the seeded medium.

It is another object of the present invention to provide a method and materials for quantitating the efficiency of decontamination by alternate waste disposal systems where, in one embodiment, a destruction-resistant medium is seeded with a number of a specific type of organisms. That medium is then added to waste and treated with waste, recovered from treated waste, and the remaining viable organisms associated with the medium cultured in a manner sufficient to detect the growth of any of the originally seeded microorganisms. In such an embodiment, the absolute presence or absence of growth reflects the absolute killing, vel non, of the seeded organisms during treatment.

In a preferred embodiment of the present invention, the seeded medium is composed of a resilient, compressible and reboundable, and porous sponge, the sponge being destruction-resistant and easily visually and tactilely identified and distinguished from the treated waste stream.

In a preferred embodiment the organisms seeded on the destruction-resistant medium are pathogen surrogates as defined in the *Technical Assistance Manual: State Regulatory Oversight of Medical Waste Treatment Technologies*, Apr. 1994, A Report of the State and Territorial Association on Alternate Treatment Technologies, herein incorporated by reference.

In a preferred embodiment the destruction-resistant seeded medium is designed to be used with all the alternate waste treatment systems described in the *Technical Assistance Manual: State Regulatory Oversight of Medical Waste Treatment Technologies*.

In a preferred embodiment the materials and methods are designed to conform with the requirements and suggestions for quality control means as set forth in the *Technical Assistance Manual: State Regulatory Oversight of Medical Waste Treatment Technologies*, including, but without limitation to, quantification, testing protocols, all levels of inactivation, all test organisms, and all technologies.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 1 shows the addition of an indicator microorganism seeded sponge to a batch of medical waste to be treated;

FIG. 2 shows the treatment of a batch of medical waste containing a seeded destruction resistant indicator medium;

FIG. 3 shows the resulting, treated product containing readily identifiable pieces of indicator containing medium; and FIG. 4 shows the recovery of the indicator medium from the treated waste.

DETAILED DESCRIPTION OF THE PREFERRED EMBODIMENT

The present invention relates to the instant invention relates to a novel method and a product for quality control in alternative, destruction-type biological decontamination and sterilization processes. The invention relates the use of a biological organism, seeded on any destruction-resistant medium, used as a quality control means for any type of decontamination and/or sterilization procedure that would otherwise destroy a traditional, nondestruction-resistant quality control means.

In a preferred embodiment of the present invention, a destruction-resistant sponge (FIG. 1) is seeded with in a known number and type of bacteria, or bacterial endospores, is used as a routine quality control means for alternate biological decontamination and/or sterilization processes. In such an embodiment, the bacteria/spore-seeded destruction-resistant sponge is added to the waste to be treated (FIG. 2) and then is processed along with the waste. The sponge material is then recovered from the treated waste by easy visual and/or tactile identification and differentiation from the treated wastes (FIGS. 3 and 4). Because of the physical properties of the sponge, including, but not limited to, tear resistance, resiliency, compressibility and reboundability, tensile strength non-britallity and resistance to physical damage in alternative type sterilization and/or decontamination processes, following treatment, the sponge can easily be distinguished from the treated wastes and thereby recovered (FIGS. 3 and 4).

In a preferred embodiment, following established protocols, (for example, those outlined in the *Oversight of Medical Waste Treatment Technologies Manual*) the number of viable bacteria (and/or bacterial spores) associated with the recovered sponge material is determined (for example, by culturing and quantitating the number of viable organisms recovered) and compared relative to an untreated, control sponge and/or the sponge before treatment. A calculation of the reduction in viable bacteria between the seeded sponge and the number on the originally untreated sponge is then used to assess (again, for example, as per the guidelines of the Technical Assistance Manual) the quality, or effectiveness, of the biological decontamination process.

In another, similar and preferred embodiment, a destruction-resistant sponge medium seeded with a known number and type of microorganisms is added to a waste treatment system and recovered post treatment, and then the recovered sponge is cultured for the presence of any growth of the specific seeded organisms; the results producing an all-or-none qualitative evaluation of the effectiveness of the waste decontamination and/or sterilization system.

In such an embodiment, the sponge can be supplied to the user along with a biological indicator medium for determining the presence or absence of microorganisms. In such a case, the sponge could be seeded with a microorganism not normally considered a background contaminant.

In this case, a sponge seeded with a known number of such organisms can be added to the waste to be treated, then recovered and the recovered sponge material added to the biological indicator medium which is specifically formulated to detect the presence of any growth of the seeded organism. Positive identification of growth would indicate that some organisms survived the decontamination and/or sterilization treatment. On the other hand, negative growth would indicate that none of the seeded organisms on the recovered sponge survived. In such a case, the effectiveness of killing (inactivation) can be calculated by the original number of organisms seeded on the sponge.

Regarding quantitation, in various embodiments, it is only necessary to recover a fraction of the total amount of seeded material in order to both qualitatively and quantitatively measure the killing effectiveness of a sterilization and/or decontamination process. As shown, for example in FIGS. 1-4, since the seeded sponge material survives the treatment process in reactively large pieces, only one, or a few pieces need be recovered in order to evaluate the percentage of viable organisms surviving the treatment process.

For example, in an embodiment of the present invention, and as described in the examples below, a sponge medium is seeded with a known number of microorganisms by having the sponge absorb completely a given volume of a broth containing a known number of microorganisms. Following this absorption step, the sponge is then dried and weighed and accordingly, is known to contain a given number of microorganisms seeded per unit volume of sponge.

Following treatment, one, or a few, pieces of sponge are removed from the treated waste (FIG. 4), dried and weighed. By comparison with the original organism/unit content, the amount of microorganisms originally provided on the recovered piece of sponge can be calculated. Subsequent quantitation of the viable microorganisms remaining on the sponge can provide either a qualitative or quantitative reading of the efficiency of the decontamination and/or sterilization process.

It is important that the indicator containing medium be destruction resistant. This can include being non-brittle, resilient, compressible, bendable, stretchable, flexible, tear resistant, breakage resistant and so forth. Further, in some embodiments of the invention it may be preferable that the medium be resistant to the heat or chemical disinfection means. In one preferred embodiment of the present invention, the medium is a nylon and cellulose containing sponge. The medium can also be composed of, for example, but not limited to, fibers that increase wet strength such as: nylon and other polyamides; polyester fibers such as dacron or celanar; polypropylene fiber; rayon fiber; polyethylene fiber; polyacrylonitrile fiber; glass fiber; asbestos fiber; and carbon fiber.

In some embodiments, it might also be preferable to have the indicator containing medium visually marked with indicia to help it to visually stand out from the treated waste. Such indicia might include distinct colors, for example, florescent colors, and/or distinct patterns.

Additional examples of various embodiments of the instant invention are given in the examples that follow below.

Underlying the development of assessment protocols for approving an emerging alternative medical waste treatment technology, is the establishment of efficacy criteria that provide a quantitative and qualitative measure of required performance. There is no consensus among the states on the level of microbial inactivation required of a medical waste treatment process. To properly define microbial inactivation requires that definitions established include both qualitative and quantitative aspects. From this perspective, definitions need to be established which qualitatively define microbial inactivation (i.e., form and type of microorganisms affected) and which quantify the required level of inactivation.

The terms sterilization and disinfection have provided some measure of prescriptive criteria as used in denoting sterilization or degree of disinfection required of medical instruments and supplies. Sterilization is commonly defined as the complete elimination or destruction of all forms of microbial life, including highly resistant bacterial endospores. Since complete elimination or destruction is difficult to prove, sterilization is usually expressed as a probability function in terms of the number of microorganisms surviving a particular treatment process. This function is usually expressed as a 6 $Log_{10}$ reduction (defined as 6 decade reduction or a one millionth [0.000001] survival probability in a microbial population; i.e., a 99.9999% reduction) of the most resistant microorganisms to the sterilization process in question. Spore suspensions of resistant Bacillus species are often used as biological indicators for determining the efficacy of the sterilization process (i.e., *B. stearothermophilus*, thermal inactivation; *B. subtilis*, chemical inactivation; *B. pumilus*, irradiation inactivation).

Disinfection can be defined as a procedure that reduces the level of microbial contamination. How disinfection is defined is dependent on the process in which the disinfectant is used, what microorganisms are affected, and what level of microbial inactivation is achieved. In one definition, disinfectants are labeled as low-intermediate- or high-level, determined in part on the survivability of microbial groups (i.e., bacterial spores [most resistant], mycobacteria, non-lipid or small viruses, fungi, vegetative bacteria, and lipid or medium-sized viruses [least resistant]) after treatment. Low-level disinfectant processes cause the death of all bacteria except *Mycobacterium tuberculosis* and *M. bovis*, lipid-enveloped and medium-sized viruses (e.g., herpes simplex virus, cytomegalovirus, respiratory syncytial virus, hepatitis B virus, and human immunodeficiency virus), and fungi. Intermediate-level disinfectant processes do not necessarily kill bacterial spores but are effective against tubercle bacillus and fungi. However, intermediate-level disinfectant processes vary in their effectiveness against viruses, with small non-lipid viruses (e.g., rhinoviruses) being significantly more resistant than medium-sized, lipid viruses. High-level disinfectant processes cause the death of all microbial life, except for high numbers of bacterial spores. Sporicidal capacity is an essential property of high-level disinfection, although the amount of sporicidal activity is not quantified in any definition.

The following categories of microbial inactivation are presented:

Level I

Inactivation of vegetative bacteria, fungi, and lipophilic viruses

Level II

Inactivation of vegetative bacteria, fungi, all viruses, and mycobacteria

Level III

Inactivation of vegetative bacteria, fungi, all viruses, mycobacteria, and *B. stearothermophilus* spores at $10^4$ or greater; or *B. subtilis* spores at $10^4$ or greater with chemical treatment Level IV Inactivation of vegetative bacteria, fungi, all viruses, and mycobacteria, and *B. stearothermophilus* spores at $10^6$ or greater The selection of pathogen surrogates representing vegetative bacteria, fungi, parasites, viruses, mycobacteria, and bacterial spores is necessary to define and facilitate any quality control process. Criteria defining surrogate selection should include that any surrogate recommended:

Not affect healthy individuals;

Be easily obtainable;

Be an ATCC registered strain, as available;

Be easily cultured and maintained; and

Meet quality control requirements.

Microorganism strains obtained from the American Type Culture Collection (ATCC) and methods prescribed by the Association of Official Analytical Chemists (AOAC) assist in fulfilling these recommendations by (1) providing traceable and pure cultures of known characteristics and concentration and (2) providing recognized culturing protocols and detailed sampling and testing protocols.

Provided in Table I are the biological indicators recommended for testing microbial inactivation efficacy in medical waste treatment processes. The selection of these representatives was based on each microorganism:

Meeting, where possible, the criteria established above;

Representing, where possible, those organisms associated with medical waste; and Providing a biological challenge equivalent to or greater than that associated with microorganisms found in medical waste.

Biological indicators selected to provide documentation of relative resistance to an inactivating agent should be chosen after evaluation of the treatment process as it relates to the conditions used during comparative resistance research studies described in the literature. Literature studies support the assertion that the degree of relative resistance of a microorganism to an inactivating agent can be dependent on various factors (i.e., pH, temperature). Conditions used in literature studies that demonstrate a relatively high degree of resistance of a particular microorganism may be significantly different to the conditions found within the treatment process. A comparison of the conditions used in the literature to those used in the treatment process should be made to determine if relative microbial resistance can be altered (i.e., lowered) as a result of treatment process conditions.

TABLE I

RECOMMENDED BIOLOGICAL INDICATORS

| | |
|---|---|
| Vegetative Bacteria | *Staphylococcus aureus* (ATCC 6538) |
| | *Pseudomonas aeruginosa* (ATCC 15442) |
| Fungi | *Candia albicans* (ATCC 18804) |
| | *Penicillium chrysogenum* (ATCC 24791) |
| | *Aspergillus niger* |
| Viruses | Polio 2, Polio 3 |
| | MS-2 Bacteriophage (ATCC 15597-B1) |
| Parasites | *Cryptosporidium* spp. oocysts |
| | *Giardia* spp. cysts |
| Mycobacteria | *Mycobacterium terrae* |
| | *Mycobacterium phlei* |
| | *Mycobacterium bovis* (BCG) (ATCC 35743) |
| Bacterial Spores | *B. stearothermophilus* (ATCC 7953) |
| | *B. subtilis* (ATCC 19659) |

It has been recommended that one or more of the representative microorganisms from each microbial group be used in efficacy evaluation. Specific criteria for the selection of these microorganisms are provided below in Table II:

TABLE II

Biological Indicator Selection Criteria

Vegetative Bacteria

*Staphylococcus aureus* and *Pseudomonas aeruginosa* were selected to represent both gram-positive and gram-negative bacteria, respectively. Both are currently required by the Association of Official Analytical Chemists (AOAC) use-dilution method and both have been shown to be resistant to chemical inactivation.

Fungi

The selection of *Candida albicans* and *Penicillium chrysogenum* was based on reported data indicating these organisms representing yeast and molds, respectively, are the most resistant to germicides. Although *Trichophyton mentagrophytes* is the AOAC test organism for molds, *Penicillium chrysogenum* is reported to be more resistant to germicides. The inclusion of *Aspergillus niger* as an indicator organism was based on its familiarity as a common mold.

Viruses

Lipophilic (enveloped) viruses are less resistant to both thermal and chemical inactivation than the hydrophilic (nonenveloped) viruses. As such, enveloped viruses such as HIV, Herpes simplex virus and Hepatitis B virus are less resistant than enveloped viruses such as Poliovirus, Adenovirus, and Coxsackievirus. Polio 2 (attenuated vaccine strain) and Polio 3 virus were selected based on their relative higher chemical and thermal resistance. Additionally, the use of an enterovirus (e.g., Polio 2 or Polio 3) can provide a stringent measure of efficacy for irradiation treatment processes. MS-2 bacteriophage was selected as a Hepatitis virus surrogate in that this bacteriophage offers a comparable degree of chemical and thermal resistance, is safe to handle and easy to culture.

Parasites

Both *Cryptosporidium* spp. occysts and. *Giardia* spp. cysts are used as test organisms to demonstrate germicidal effectiveness. Cryptosporidium has been demonstrated to have a higher chemical resistance and *Cryptosporidium* spp. oocysts are more readily available than *Giardia* spp. cysts. Both are significantly pathogenic (both have an infectious dose of 10 cysts) and care is advised when using these microorganisms as parasitic biological indicators.

Mycobacteria

*Mycobacterium phlei* has a demonstrated measure of disinfectant resistance, is a rapid grower and is pigmented for easy identification. *M. bovis* (BCG) is used in the AQAC Tuberculocidal Method and is analogous to *M. tuberculosis* in that it is in the same group or complex. Individuals exposed to *M. bovis* (BCG,ATCC strain) may skin test convert although no actual infectivity or disease occurs. Risk of exposure would come from those mechanisms that grind the waste. *Mycobacterium terrae* is equivalent to *M. tuberculosis* in resistance to chemical inactivation. In Europe it is recommended for disinfectant testing.

Bacterial Spores

Both *B. stearothermophilus* and *B. subtilis* spores are commonly used as biological indicators for both thermal and chemical resistance. *B. stearothermophilus* spores exhibit more thermal and chemical resistance than spores from *B. subtilis*.

Establishing the mechanisms to quantify the level of microbial inactivation is essential in developing the format and requirements of the guidance protocols. As presented and discussed, microbial inactivation ("kill") is equated to "$Log_{10}Kill$" which is defined as the difference between the logarithms of number of viable test microorganisms before and after treatment. This definition is translated into the following formula:

$$Log_{10}Kill = Log_{10}(cfu/g\ Introduced) - Log_{10}(cfu/g\ Recovered)$$

where:

$Log_{10}Kill$ is equivalent to the term $Log_{10}$ reduction;

"Introduced" is the number of viable test microorganisms introduced into the treatment unit;

"Recovered" is the number of viable test microorganisms recovered after treatment; and "cfu/g" are colony forming units per gram of waste solids. A $Log_{10}Kill$ of 6 or greater is equivalent or less than a one millionth [0.000001] survival probability in a microbial population or a 99.0000% reduction or greater of that population.

Using the Level III definition, a $Log_{10}Kill$ of 6 (e.g., 6 $Log_{10}$ reduction) is required of vegetative bacteria, fungi, lipophilic/hydrophilic viruses, parasites, and mycobacteria and a $Log_{10}Kill$ of 4 (e.g., 4 $Log_{10}$ reduction) is required of *B. stearothermophilus* or *B. subtilis* spores. Employing the above equation to quantify microbial inactivation will require the consideration of the methods of biological indicator introduction and recovery.

Quantitative measurement of efficacy can involve, for example, a two-step approach. The purpose of the first step may be to account for the reduction of microorganisms due to equipment design (i.e., dilution of indicator organisms or physical entrapment).

This first step, the "Control", is typically performed using microbial cultures (i.e., liquid suspensions) of predetermined concentrations necessary to ensure a sufficient microbial recovery at the end of the step. The microbial suspension is added to a standardized microbial recovery at the end of this step. The microbial suspension is added to a standardized surrogate medical waste load that is processed under normal operating conditions without the addition of the microbial inactivation agent (i.e., high moisture content, high organic load, high density) required of the equipment. After processing, waste samples are collected and washed to recover the biological indicator organisms in the sample. Recovered microorganism suspensions are plated to quantify microbial recovery. The number of viable microorganism recovered serves as a baseline quantity for comparison to the number of recovered microorganisms from wastes processed with the microbial inactivation agent. The required number of recovered viable indicator microorganisms from the "Control" must be equal to or greater than the number of microorganisms required to demonstrate the prescribed Log reduction as defined in Level III (i.e., a 6 $Log_{10}$ reduction for vegetative microorganisms and a 4 $Log_{10}$ reduction for spores).

This step can be defined by the following equation:

$$Log_{10}RC = Log_{10}IC - Log_{10}NR$$

where:

$Log_{10}RC$ is the number of viable "Control" microorganisms (in colony forming units per gram of waste solids) recovered in the non-treated processed waste residue;

$Log_{10}IC$ is the number of viable "Control" microorganisms (in colony forming units per gram of waste solids) introduced into the treatment unit; and $Log_{10}NR$ is the number of "Control" microorganisms (in colony forming units per gram of waste solids) not recovered in the non-treated processed waste residue.

Rearranging the equation above enables the calculation of microbial loss due to dilution, physical manipulation, or residue adhesion during the treatment process. $Log_{10}NR$ represents an accountability factor for microbial loss and is defined by the following equation:

$$Log_{10}NR = Log_{10}IC - Log_{10}RC$$

The second step ("Test") is to operate the treatment unit as in the "Control" run with the selected biological indicators, but with the addition of the microbial inactivation agent. After processing, waste samples are collected and washed as in the "Control" to recover any viable biological indicator organisms in the sample. From data collected from the "Test" and "Control", the level of microbial inactivation (i.e., "$Log_{10}Kill$") can be calculated by employing the following equation:

$$Log_{10}Kill = Log_{10}IT - Log_{10}NR - Log_{10}RT$$

where:

$Log_{10}Kill$ is equivalent to the term $Log_{10}$ reduction;

$Log_{10}IT$ is the number of viable "Test" microorganisms (in colony forming units per gram of waste solids) introduced into the treatment unit. $Log_{10}IT = Log_{10}IC$;

$Log_{10}NR$ is the number of "Control" microorganisms (in colony forming units per gram of waste solids) not recovered in the non-treated processed waste residue; and $Log_{10}RT$ is the number of viable "Test" microorganisms (in colony forming units per gram of waste solids) recovered in treated processed waste residue.

The following Examples are intended to illustrate the embodiments of the present invention and are not in any way intended to limit the scope of the invention in any manner.

EXAMPLE 1

Microbial Inactivation Testing Protocol Example 1

Materials

Cellulose and nylon sponge;

*B. subtilis;*

TSB (tryptic soy broth) Broth;

CIDEX (sporocidal);

nutrient plates.

Procedure

1. A cellulose and nylon sponge is cut into about 24 equal pieces, each being a cube of about ⅛"–½" and weighing about 0.5 grams each.

2. Each piece of sponge is saturated with a late log phase solution of *B. subtilis* (*B. subtilis* grown in TSB broth at 35° C. for 24 to 48 hours and containing about $2.5 \times 10^7$ c.f.u. (colony forming units) per ml, about 2.5 ml per piece of sponge). Saturated sponges can be used immediately, or stored, lyophilized and stored, or frozen and stored before use.

3. Four pieces of saturated sponge are added to each of two tubes (for example, 50 ml conical tubes), a control tube and a treatment tube.

4. At time zero, one piece of sponge is removed from each tube and the cfu in the sponge is assayed as described below in step 7.

5. At time zero, an amount of TSB is added to sufficiently cover the sponges in the control tube and an amount of CIDEX is added to sufficiently cover the sponges in the treatment tube.

6. For a time of up to one hour, conditions that simulate the conditions in alternative destruction-type waste treatment systems are produced for both tubes, including vigorous vortexing and shaking of the tubes. At each of 5, 15, and 60 min. one piece of sponge is removed from the tubes and assayed as described below in step 7.

7. For each piece of sponge removed from the tubes as described above, an amount of liquid is expressed from the sponge, diluted 1:100 with TSB, plated on nutrient agar and the resulting colonies, if any, recorded and calculated.

8. Table III shows the results of the above described experiment. Importantly, it shows that even 5 min. exposure to CIDEX results in an assayable reduction in colony forming units of at least four orders of magnitude. Also importantly, the control shows that after time zero, a consistently identifiable and reproducible level of colony forming units remain associated with the sponge despite the simulated destruction-type treatment conditions.

TABLE 3

Treatment and control under simulated destruction-type conditions

| Time | Treatment | Control |
| --- | --- | --- |
| 0 min. | $3.0 \times 10^4$ cfu/ml | $3.4 \times 10^4$ cfu/ml |
| 5 min. | 0 | $1.5 \times 10^4$ cfu/ml |
| 15 min. | 0 | $1.7 \times 10^4$ cfu/ml |
| 60 min. | 0 | $1.6 \times 10^4$ cfu/ml |

EXAMPLE 2

Preparation of Indicator Seeded Medium

Materials

Cellulose and nylon sponge;

B. subtilis;

TSB Broth.

Procedure

1. A culture of indicator bacteria (e.g., but not limited to, B. subtilis, M. bovis, and B. stearothermophilus) is grown in nutrient broth to late log or stationary phase and the number of cfu/ml quantitated by ordinary techniques in the art. The concentration of bacteria and/or spores may then be increased in the solution by conventional means known in the art such as by centrifugation, ultrafiltration, precipitation and so forth.

2. A number of cellulose and nylon sponges are saturated with the bacteria and/or sponge containing solution to form a lot of indicator seeded sponges. The number of cfu per unit of sponge in a lot is then calculated based upon the volume of solution absorbed per unit of sponge. The cfu per unit volume of sponge can range from about $1.0 \times 10^4$ cfu per 0.1 g of sponge to about $1.0 \times 10^4$ cfu per 0.5 g of sponge to about $1.0 \times 10^{13}$ cfu per 0.1 g of sponge to about $1.0 \times 10^{13}$ cfu per 0.5 g of sponge.

3. Sponges from the lot are packaged for distribution, storage and/or subsequent use. For example, sponges may be dried, freeze dried (lyophilized) or frozen prior to packaging. Packaging may include sealing the indicator organism containing sponge in a container such as, but not limited to, an aluminum foil pouch which may be, for example, under vacuum seal.

4. Samples of packaged sponges from each lot are then tested as controls in the various destruction-type alternative waste treatment systems commonly used in the industry. For each type system and each lot of sponges, samples of packaged sponge are run through the system without the disinfecting, decontamination or sterilization step and the number of cfu per unit volume of sponge after treatment is quantitated in order to determine, as a control, the number of viable cfus that will remain on the sponge without disinfection, decontamination or sterilization. This control number, usually in the range of between about $1.0 \times 10^4$ cfu/0.1 g sponge to $1.0 \times 10^{13}$ s/0.1 g sponge, is then supplied to consumers with the each packaged sponge lot to serve as a control number.

EXAMPLE 3

Use of Seeded Indicator Medium With Quantitation

Materials

Cellulose and nylon sponge seeded with B. subtilis, M. bovis, B. stearothermophilus or other suitable indicator microorganism.

TSB Broth and nutrient plates.

Procedure

1. A sponge seeded with indicator organisms, for example, a packaged sponge as described in Example 2 above, is added to waste to be treated by a nonconventional destruction type waste treatment system (see, for example, FIG. 1).

2. Following treatment of the sponge containing waste (for example, as shown in FIGS. 2 and 3), a sufficient amount of the sponge is removed from the treated waste and measured (see, for example, FIG. 4). Due to, inter alia, the non-brittle, resilient, and tear-resistant nature of the sponge, following treatment the sponge can easily be identified and distinguished from the treated waste thus facilitating easy recovery (see, for example, FIG. 4). In some embodiments, identifying indicia on the sponges, such as distinct color or pattern, may also aid in the easy visual identification of the medium in the treated waste stream.

2. Following recovery, the sponge recovery may be determined by, for example, weight or volume. A small amount of liquid in the recovered sponge is then expressed and plated in various dilutions (see, for example, Example 1, a 1:100 dilution) and plated on nutrient plates to determine the cfu/unit of sponge remaining following treatment.

3. The amount of sterilization, disinfection or decontamination is then determined by comparing the results (cfu/unit vol) of the treated sponge with those of the control sponge (as determined by, for example, as shown in Example 2, or, for example, as compared to a control run directly in the treatment system but without a decontamination step). The reduction in the cfu/unit vol. of the treated versus control sponge indicating the effectiveness of the treatment system.

In varying embodiments of this system, the sponges may be sold, for example, in a kit complete with equipment and materials for making dilutions and plating to quantitate the remaining organisms, or with equipment and materials necessary to send the recovered, treated sponges to a laboratory in order to be quantitated.

In another embodiment of the present invention, the quantitation step may specifically be able to identify the cultured organisms as those resulting from the organisms originally seeded on the sponge. Such an embodiment may include heat incubation where the indicator organisms are heat-resistant (e.g., B. stearothermophilus), or other screening or selecting means for traits of the indicator organisms such as, but not limited to, antibiotic resistance, specific enzymatic features and phage resistance. Note that such specific features of the indicator organisms may be naturally present in the organisms (e.g., heat resistance of B. stearothermophilus) or genetically engineered in the indicator organisms (e.g., transformation with antibiotic resistance gene containing plasmids).

EXAMPLE 4

Use Of Seeded Indicator Medium With Qualitation

Materials

Cellulose and nylon sponge seeded with B. subtilis, M. bovis, B. stearothermophilus or other suitable indicator microorganism at a known number of cfu per unit sponge;

Indicator broth.

Procedure

1. A sponge seeded with a known number of indicator organisms, for example, a packaged sponge as described in Example 2 above, is added to waste to be treated by a nonconventional destruction type waste treatment system (see, for example, FIG. 1).

2. Following treatment of the sponge containing waste (for example, as shown in FIGS. 2 and 3), a sufficient amount of the sponge is removed from the treated waste and measured (see, for example, FIG. 4). It is important to recover a sufficient volume of sponge so that the recovered volume in untreated controls would yield a minimum number of viable cfus in order to satisfy quantitation requirements. For example, if it is desirable to show a four order of magnitude drop in viability upon treatment, the amount of sponge used would be such that the amount of sponge recovered following treatment would yield a recovery of about $10^4$ cfu in a unsterilized or undisinfected control. In this way, a qualitative result of no growth where the medium would have contained at least $10^4$ cfu if not treated, indicates that the treatment reduced the viability of organisms in the treated waste by at least four orders of magnitude.

3. The recovered sponge is then added to a growth medium and assayed to determine the presence or absence of growth of indicator organisms. Absence of growth indicates that at least the control number of cfu/unit sponge have been killed.

In an embodiment of the system, sponges may be sold, for example, in a kit complete with equipment and materials for qualitating the presence or absence of growth of the indicator organisms. Also, in another embodiment of the present invention, the qualitation step may specifically be able to identify the cultured organisms as those resulting from the organisms originally seeded on the sponge. Such an embodiment may include heat incubation where the indicator organisms are heat-resistant (e.g., *B. stearothermophilus*), or other screening or selecting means for traits of the indicator organisms such as, but not limited to, antibiotic resistance, specific enzymatic features and phage resistance. Note that such specific features of the indicator organisms may be naturally present in the organisms (e.g., heat resistance of *B. stearothermophilus*) or genetically engineered in the indicator organisms (e.g., transformation with antibiotic resistance gene containing plasmids).

EXAMPLE 5

Demonstration Of Control

Materials

Cellulose and nylon sponges seeded with *M. bovis* indicator microorganisms;

Nutrient plates.

Procedure

The following experiment was performed as a control in order to be certain that a sufficient number of indicator microorganisms (a minimum generally of at least approximately $1.0\times10^4$ cfu/unit sponge) remain associated with a control sponge run through an alternative type disinfection/sterilization system without the sterilization/disinfection step.

As discussed above, generally at least about $1.0\times10^4$ cfu of indicator organisms per measurable/recoverable unit of sponge should remain associated with the sponge following control treatment (i.e., treatment identical to all of the physical conditions of actual disinfection/sterilization but without the organism killing/inactivation step). This allows an extrapolation from the results with a treated sponge, allowing one to determine that the treatment killed or inactivated at least a given number of organisms that would have otherwise have been present per unit of sponge. As discussed above, when the control number of indicator microorganisms per recoverable/measurable unit of control sponge is at least $1.0\times10^4$ cfu, then if treatment, for example, kills or inactivates all organisms on a unit of treated sponge, one can conclude, for example, that the treatment killed or inactivated at least $1.0\times10^4$ cfu per unit of sponge. As discussed above, a determination of this level of killing or inactivation is generally acceptable evidence of proper sterilization and/or disinfection for an alternative type waste treatment system.

1. Cellulose and nylon sponges seeded with *M. bovis* indicator microorganisms from a late log phase culture, as described above, are added to at least two different batches of representative types of medical waste (different compositions of solids and liquids) to be treated with an alternative type waste treatment system (in this case, for example, a chemical type disinfection system manufactured and sold by Premier Medical Technologies, Inc., Houston Tex.).

2. The sponges in the batches of medical waste are then run through the treatment system under normal treatment conditions but without the addition of the chemical disinfectant.

3. Units of treated sponge (0.1 g) are then recovered and the number of cfu/unit determined via conventional microbial techniques (see above).

Results

Test A

Following control treatment: $1.0\times10^4$ cfu of indicator microorganisms remained per unit (0.1 g) of recovered control sponge.

Test B

Following control treatment: $6.0\times10^4$ cfu of indicator microorganisms remained per unit (0.1 g) of recovered control sponge.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method for quality control of infectious waste decontamination processes, which involve a step of disrupting the waste in the treatment process, comprising the steps:

a) providing a destruction resistant medium seeded with indicator microorganisms at a given number per unit, said microorganisms being homogeneously seeded throughout the entirety of said medium, such that the number of microorganisms per given unit of medium is substantially constant throughout the entirety of the medium;

b) adding said medium to infectious waste to be treated;

c) treating said waste with at least one step of physically disrupting the waste;

d) during the treatment of said waste, physically severing said medium into at least two separate pieces;

e) recovering at least a portion of said medium from said treated waste; and f) testing for the presence of viable indicator microorganisms on the treated medium.

2. The method of claim 1, wherein the number of viable indicator microorganisms remaining on the recovered destruction resistant medium is quantitated following waste treatment.

3. The method of claim 2, wherein the recovered destruction resistant indicator medium is squeezed to express fluid and that fluid is then plated in order to quantitative the number of viable microorganisms.

4. The method of claim 2, where the quantification step specifically identifies the indicator microorganisms.

5. The method of claim 1, where the destruction resistant medium is a sponge.

6. The method of claim 1, where the destruction resistant medium is a cellulose and nylon containing sponge.

7. The method of claim 1, wherein the indicator microorganisms are selected from the group consisting of *B. subtilis*, *B. stearothermophilus* and *M. bovis*.

8. The method of claim 1, wherein the said recovered destruction resistant medium is assayed qualitatively for the all or none presence of viable indicator microorganisms remaining on the recovered destruction resistant medium following waste treatment.

9. The method of claim 8, where the qualification step specifically identifies the indicator microorganisms.

10. A method for quality control of infectious waste decontamination processes, which involve a step of disrupting the waste in the treatment process, comprising the steps:

a) providing a destruction resistant medium seeded with indicator microorganisms at a given number per unit, said microorganisms being homogeneously seeded throughout the entirety of said medium, such that the number of microorganisms per given unit of medium is substantially constant throughout the entirety of the medium;

b) adding said medium to infectious waste to be treated;

c) treating said waste with at least one step of physically disrupting the waste;

d) during the treatment of said waste, physically severing said medium into at least two separate pieces;

e) recovering at least a portion of said medium from said treated waste;

f) recovering viable indicator microorganisms from said recovered medium;

g) detecting the number or presence of said indicator microorganisms on said recovered medium.

\* \* \* \* \*